United States Patent [19]
Gelfand et al.

[11] Patent Number: 6,132,978
[45] Date of Patent: Oct. 17, 2000

[54] METHOD TO REGULATE CD40 SIGNALING

[75] Inventors: Erwin W. Gelfand, Englewood; Gary L. Johnson, Boulder, both of Colo.

[73] Assignee: National Jewish Medical and Research Center, Denver, Colo.

[21] Appl. No.: 08/769,747

[22] Filed: Dec. 19, 1996

Related U.S. Application Data

[60] Provisional application No. 06/008,877, Dec. 19, 1995.

[51] Int. Cl.$^7$ .................. G01N 33/53; G01N 33/367; G01N 33/574; G01N 33/573
[52] U.S. Cl. .................. 435/7.2; 435/7.21; 435/7.23; 435/7.24; 435/7.4; 435/7.8; 436/63
[58] Field of Search .................. 435/7.2, 7.21, 435/7.23, 7.24, 7.4, 7.8, 975; 436/63, 808; 514/2, 23, 44, 8

[56] References Cited

U.S. PATENT DOCUMENTS

| | | | |
|---|---|---|---|
| 5,540,926 | 7/1996 | Aruffo et al. | 424/153.1 |
| 5,605,808 | 2/1997 | Karin et al. | 435/15 |
| 5,674,492 | 10/1997 | Armitage et al. | 424/144.1 |

OTHER PUBLICATIONS

Ishizuka et al., "Aggregation of the FceRI on Mast cells stimulates c–Jun Amino–terminal kinase activity" J. Biol. Chem. vol. 271. No. 22. pp. 12762–12766 May 31, 1996.

Bagrodia et al., 1995, *J. Biol. Chem*, 270:27995–27998.
Faris, et al., 1994, *J. Exp. Med.*, 179:1923–1931.
Gallop, et al., 1994, *J. Med. Chem.*, 37:1233–1251
Han, et al., 1995, *Biochim. Biophys. Acta.*, 1265:224–227.
Kallunki, et al., 1994, *Genes and Development*, 8:2996–3007.
Kharbanda, et al., 1995, *Nature*, 376:785–788.
Kramer, et al., 1995, *J. Biol. Chem.*, 46:27395–27398.
Kumar, et al., 1995, *J. Biol. Chem.*, 46:27905–27913.
Landry, et al., 1995, *Biochem. Cell. Biol.*, 73:703–707.
Raingeaud, et al., 1993, *J. Biol. Chem.*, 270:7420–7426.
Raitano, et al., 1995, *Proc. Natl. Acad. Sci. USA*, 92;11746–11750.

*Primary Examiner*—Yvonne Eyler
*Attorney, Agent, or Firm*—Sheridan Ross P.C.

[57] ABSTRACT

The present invention relates to methods useful for identifying compounds capable of specifically controlling CD40 regulation of JNK or p38 activity useful for inhibiting immunoglobulin heavy chain class switching, cytokine production and activation of cells involved in an inflammatory response. The present invention also includes kits to perform such assays and methods to control disease related to such responses.

9 Claims, 7 Drawing Sheets

METHOD TO REGULATE CD40 SIGNALING

CROSS REFERENCE TO RELATED APPLICATIONS

The present application claims priority from U.S. Provisional application Ser. No. 60/008,877, filed Dec. 19, 1995.

GOVERNMENT RIGHTS

This invention was made in part with government support under DK-37871 and GM-30324, both awarded by the National Institutes of Health. The government has certain rights to this invention.

FIELD OF THE INVENTION

The present invention relates to a process for identifying compounds that control CD40 regulation of Jun kinase and p38 MAP kinase activity. The present invention also relates to a method to treat allergies and autoimmunity by regulating the activity of Jun kinase and p38 MAP kinase in a cell.

BACKGROUND OF THE INVENTION

The B lymphocyte surface antigen receptor membrane immunoglobulin has important functions in the binding and internalization of antigen, as well as in transducing signals through the plasma membrane which lead to cell activation, differentiation and apoptosis. Crosslinking of the receptor stimulates the Ras/Raf-1/MEK cascade with activation of $p42^{erk2}$ MAPK and $p90^{rsk}$. A second important B cell surface antigen receptor is CD40. CD40 is a 45–50 kD transmembrane glycoprotein expressed on all mature B cells. CD40 is a member of the TNF receptor family and has homology to the receptors for nerve growth factor, TNF-α, Fas and CD30. The ligand for CD40 (CD40 L, gp39) is expressed on activated T lymphocytes and activation through CD40 plays an important role in T cell-dependent immunoglobulin isotype switching. The signal transduction pathways through CD40 are not well delineated.

Certain biological functions of a B lymphocyte (B cell) are tightly regulated by signal transduction pathways within B cells. Signal transduction pathways maintain the balanced steady state functioning of a cell. Disease states can arise when the steady state function of a cell becomes harmful to an animal. For example, allergic reactions occur due to undesired production of IgE antibodies specific for an antigen. In addition, autoimmunity can occur due to an animal mounting an undesired immune response against a self-antigen. Signal transduction pathways in a cell can be responsible for regulating cellular biological functions. As such, regulation of signal transduction pathways can assist in the regulation of undesired cellular biological functions.

Despite a long-felt need to understand and discover methods for regulating cells involved in various disease states, the complexity of signal transduction pathways has precluded the development of products and processes for regulating cellular function by manipulating signal transduction pathways in a cell. As such, there remains a need for products and processes that permit the implementation of predictable controls of signal transduction in cells, thus enabling the treatment of various diseases that are caused by undesired cellular function.

SUMMARY OF THE INVENTION

The present invention provides a solution to the complex problem of identifying regulatory compounds which can be used to regulate cellular function, including CD40 regulation of Jun kinase (JNK) and p38 MAP kinase (p38) activity. Despite the complexity of signal transduction networks in cells, the present invention provides for an efficient method for regulating JNK or p38 activity and identifying compounds capable of specifically regulating JNK or p38 activity.

The present invention is particularly advantageous because it provides for a method to identify compounds that can regulate the production of IgE by an animal without substantially interfering with the production of IgG and IgA by an animal. As such, unlike traditional immunosuppressive reagents which suppress an animal's immune response indiscriminantly, a compound identified by a method of the present invention enables an animal to mount an immune response against foreign pathogens by producing IgG and IgA antibodies. Thus, those of skill in the art will immediately recognize the advantages arising from this invention which include the identification and uses of compounds which are useful for the treatment of allergic and autoimmune diseases but not disruptive to an animal's overall immune response.

One embodiment of the present invention includes a method to identify a compound that controls CD40 regulation of Jun kinase (JNK) activity in a cell, comprising: (1) contacting a cell with a putative regulatory compound, wherein the cell includes a CD40 protein and a Jun kinase protein; and (2) assessing the ability of the putative regulatory compound to regulate the activity of the Jun kinase. Another embodiment of the present invention includes a method to identify a compound that controls CD40 regulation of p38 activity in a cell, comprising: (1) contacting a cell with a putative regulatory compound, wherein the cell includes CD40 protein and p38 protein; and (2) assessing the ability of the putative regulatory compound to regulate the activity of the p38 protein. In particular, these methods of the present invention include a step of stimulating the cell, prior to the assessing step, with a ligand of CD40.

Also included in the present invention is a regulatory compound identified by said compound's ability to regulate a biological function selected from the group consisting of immunoglobulin heavy chain class switching, cytokine production and inflammatory cell activation, the compound being capable of penetrating the plasma membrane of a cell and of inhibiting the ability of CD40 protein to regulate JNK protein or p38 activity in the cell.

The present invention includes a method to inhibit immunoglobulin heavy chain class switching, comprising inhibiting the activity of a protein selected from the group consisting of Jun kinase protein and p38 protein. The present invention also includes a method to inhibit cytokine production by a cell having CD40, comprising inhibiting the activity of a protein selected from the group consisting of Jun kinase protein and p38 protein.

One aspect of the present invention includes a method to treat an animal with a disease selected from the group consisting of a disease involving an allergic response and an autoimmune disease, said method comprising administering to an animal an effective amount of a therapeutic composition comprising a compound that controls CD40 regulation of the activity of a protein selected from the group consisting of Jun kinase and p38 protein.

Another aspect of the present invention includes a kit to identify compound that controls CD40 regulation of JNK or p38 activity in a cell, the kit comprising: (1) a cell comprising a CD40 protein, and a Jun kinase or a p38 protein; and (2) a means for detecting regulation of the Jun kinase or p38 protein.

DETAILED DESCRIPTION OF THE INVENTION

Figure 1:
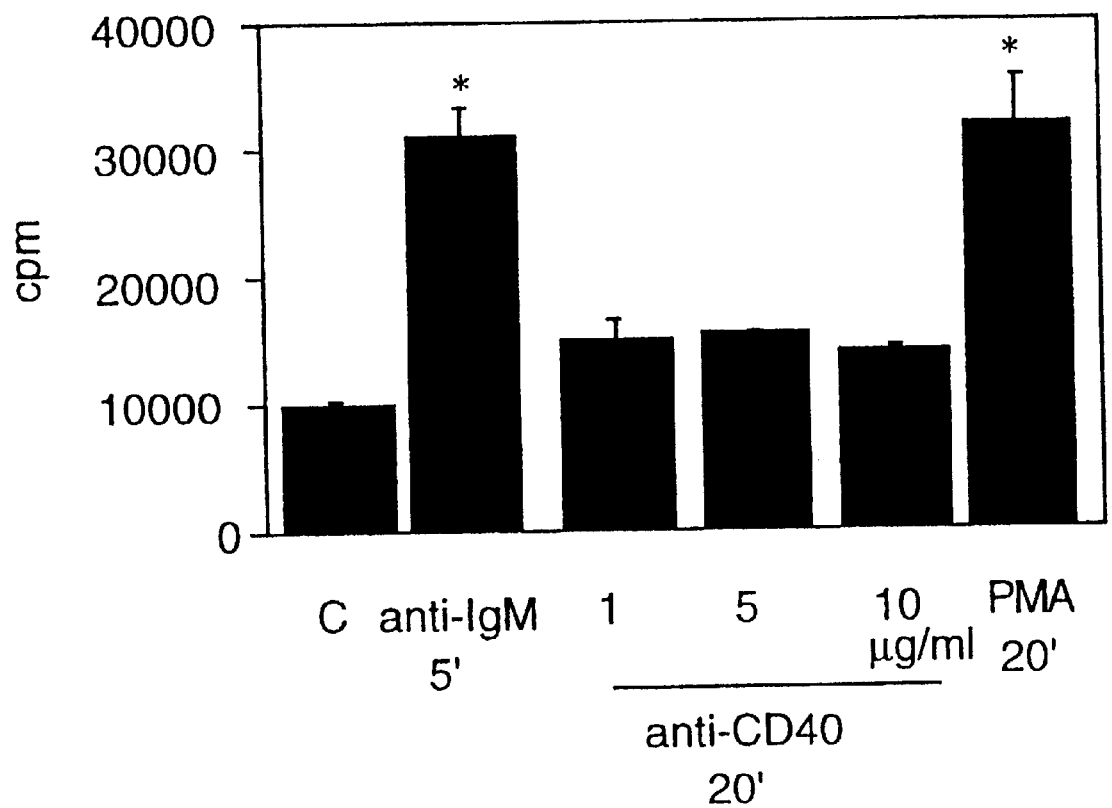
FIG. 1 illustrates the activation of ERK protein following treatment with anti-IgM antibody but not after treatment with anti-CD40 antibody.

The present invention relates to a method for identifying compounds that regulate CD40 regulation of JNK or p38 activity and products identified using such method. As used herein, the phrase "signal transduction pathway" refers to at least one biochemical reaction, but more commonly a series of biochemical reactions, which result from interaction of a cell with a stimulatory compound. The interaction of a stimulatory compound with a cell generates a "signal" that is transmitted through a signal transduction pathway, ultimately resulting in JNK or p38 activation. Compounds inhibitory to signal transduction pathways (antagonists) are also useful and can be identified by the methods of the present invention.

A signal transduction pathway of the present invention can include a variety of signal transduction molecules that play a role in the transmission of a signal from one portion of a cell to another portion of a cell. As used herein, the term "molecule" refers to a protein, a lipid, a nucleic acid or an ion, and at times is used interchangeably with such terms. In particular, a signal transduction molecule refers to a protein, a lipid, a nucleotide, or an ion involved in a signal transduction pathway. signal transduction molecules of the present invention include, for example, cell surface receptors and intracellular signal transduction molecules. As used herein, the phrase "cell surface receptor" includes molecules and complexes of molecules capable of receiving a signal and the transmission of such a signal across the plasma membrane of a cell. The phrase "intracellular signal transduction molecule," as used herein, includes those molecules or complexes of molecules involved in transmitting a signal from the plasma membrane of a cell through the cytoplasm of the cell, and in some instances, into the cell's nucleus. The phrase "stimulatory compound", as used herein, includes ligands capable of binding to cell surface receptors to initiate a signal transduction pathway, as well as intracellular initiator molecules capable of initiating a signal transduction pathway from inside a cell.

One aspect of the present invention includes a cell-based assay to identify compounds, referred to herein as "putative regulatory compounds", which are capable of regulating CD40 regulation of JNK or p38 activity. As used herein, the term "putative" refers to compounds having an unknown or previously unappreciated regulatory activity in a particular process. As such, the term "identify" is intended to include all compounds, the usefulness of which as a regulatory compound of JNK activity is determined by a method of the present invention.

One embodiment of the present invention relates to a method to identify a compound that controls CD40 regulation of JNK activity in a cell, comprising: (1) contacting a cell with a putative regulatory compound, wherein the cell includes a CD40 protein and a Jun kinase (JNK) protein; and (2) assessing the ability of the putative regulatory compound to regulate the activity of the Jun kinase. The assessment step preferably involves determining the phosphorylation of JNK upon ligation of the CD40 using antibodies specific for CD40 and/or CD40 ligand (gp39; described in Noelle et al., Proc. Natl. Acad. Sci. USA 89:6550–6554, 1992). JNK regulates the activity of the transcription factor JUN which is involved in controlling the growth and differentiation of different cell types, such as B cells, T cells, neural cells or fibroblasts. JNK is a member of the Ras signal transduction pathway, which includes molecules such as MEKK protein Jun, ATF and Myc protein.

Another embodiment of the present invention relates to a method to identify a compound that controls CD40 regulation of p38 activity in a cell, comprising: (1) contacting a cell with a putative regulatory compound, wherein the cell includes a CD40 protein and a p38 protein; and (2) assessing the ability of the putative regulatory compound to regulate the activity of the p38.

The present method can further comprise assessing the ability of a putative regulatory compound to inhibit: immunoglobulin heavy chain class switching in a cell; cytokine production by a cell; or activation of inflammatory cells (i.e., cells involved in an inflammatory response). Methods for determining immunoglobulin heavy chain class switching are to those of skill in the art. For example, Southern blots can be performed using DNA probes specific for genes encoding different classes of immunoglobulin heavy chains to look for rearrangement of the DNA encoding the different classes. Alternatively, immunoassays can be performed on proteins produced by the treated cell using antibodies specific for different classes of immunoglobulin heavy chains. Methods for determining cytokine production are known to those of skill in the art. For example, cell responsiveness assays using cells capable of responding to a cytokine can be used to test the disruption of cytokine production by a putative regulatory compound. In addition, immunoassays using antibodies specific for a cytokine can be used to test the disruption of cytokine production by a putative regulatory compound. Methods for determining inhibition of inflammatory cell activation are known to those of skill in the art by testing the ability of an inflammatory cell to perform a desired biological function in the presence or absence of a putative regulatory protein.

Suitable cells for use with the present invention include any cell that has CD40, and JNK or p38 protein. Such cells can include normal cells or transformed cells (i.e., with a heterologous nucleic acid molecule) that express CD40, and JNK and/or p38 in a native physiological context (e.g., Pre-B cells, B lymphocytes, cancer cells, fibroblasts, Langerhans cells, epithelial cells monocytes and dendritic cells). Alternatively, cells for use with the present invention can include spontaneously occurring variants of normal cells, or genetically engineered cells, that have altered signal transduction activity, such as enhanced responses to particular ligands. Signal transduction variants of normal cells can be identified using methods known to those in the art. For example, variants can be selected using fluorescence activated cell sorting (FACS) based on the level of calcium mobilization by a cell in response to a ligand. Genetically engineered cells can include recombinant cells of the present invention (described in detail below) that have been transformed with, for example, a recombinant molecule encoding a signal transduction molecule of the present invention.

Cells for use with the present invention include mammalian, invertebrate, plant, insect, fungal, yeast and bacterial cells. Preferred cells include mammalian, amphibian and yeast cells. Preferred mammalian cells include primate, non-human primate, mouse and rat, with human cells being preferred.

In one embodiment, a cell suitable for use in the present invention has a functional CD40 on the surface of the cell. A functional CD40 can comprise a full-length or a portion of a CD40 that is capable of transmitting a signal across the plasma membrane of a cell, upon ligation with an anti-CD40 antibody or a CD40 ligand, in such a manner that immunoglobulin heavy chain class switching results. Preferably, a cell of the present invention expresses a CD40 derived from a human, mouse or rat, with human cells being preferred.

In another embodiment, a cell suitable for use in the present invention has one or more intracellular signal transduction molecules capable of transmitting a signal through the cytoplasm of the cell, resulting in JNK and/or p38 activation. An intracellular signal transduction molecule as described herein can be produced in a cell by expression of a naturally occurring gene and/or by expression of a heterologous nucleic acid molecule transformed into the cell.

A preferred cell of the present invention has, amongst other signal transduction molecules, MEKK protein, Jun, ATF Myc protein, p38, phosphotidylinositol-3 kinase (PI-3 kinase), Jun kinase kinase (JNKK), Elk-1 and other Ets family members, phospholipase C γ (PLCγ) and intracellular calcium.

In a preferred embodiment, a cell for use with the present invention includes the human Burkitt's lymphoma cell line, Ramos.

Signal transduction molecules referred to herein include the natural full-length protein, or can be a functionally equivalent protein in which amino acids have been deleted (e.g., a truncated version of the protein), inserted, inverted, substituted and/or derivatized (e.g., phosphorylated, acetylated, glycosylated, carboxymethylated, myristoylated, prenylated or palmitoylated amino acids) such that the modified protein has a biological activity and/or function substantially similar to that of the natural protein. Modifications can be accomplished by techniques known in the art, including, but not limited to, direct modifications to the protein or modifications to the gene encoding the protein. Such modifications to the gene encoding the protein can include using, for example, classic or recombinant DNA techniques to effect random or targeted mutagenesis (see, for example, Sambrook et al., *Molecular Cloning: A Laboratory Manual*, Cold Spring Harbor Labs Press, 1989, which is incorporated herein by reference in its entirety).

Functionally equivalent proteins can be selected using assays established to measure the biological activity of the protein. For example, a functionally equivalent cell surface receptor would have a similar ability to bind a particular ligand as would the corresponding natural cell surface receptor protein. As a further example, a functionally equivalent intracellular signal transduction protein would have a similar ability to associate with and regulate the activity of another intracellular molecule as would the corresponding natural intracellular signal transduction protein.

In certain embodiments, a cell of the present invention is transformed with at least one heterologous nucleic acid molecule. A nucleic acid molecule as described herein can be DNA, RNA, or hybrids or derivatives of either DNA or RNA. Nucleic acid molecules as referred to herein can include regulatory regions that control expression of the nucleic acid molecule (e.g., transcription or translation control regions), full-length or partial coding regions, and combinations thereof. It is to be understood that any portion of a nucleic acid molecule can be produced by: (1) isolating the molecule from its natural milieu; (2) using recombinant DNA technology (e.g., PCR amplification, cloning); or (3) using chemical synthesis methods. A gene includes all nucleic acid sequences related to a natural cell surface receptor gene such as regulatory regions that control production of a cell surface receptor encoded by that gene (such as, but not limited to, transcription, translation or post-translation control regions) as well as the coding region itself.

A nucleic acid molecule can include functional equivalents of natural nucleic acid molecules encoding a protein. Functional equivalents of natural nucleic acid molecules can include, but are not limited to, natural allelic variants and modified nucleic acid molecules in which nucleotides have been inserted, deleted, substituted, and/or inverted in such a manner that such modifications do not substantially interfere with the nucleic acid molecule's ability to encode a molecule of the present invention. Preferred functional equivalents include sequences capable of hybridizing under stringent conditions (i.e., sequences having at least about 70% identity), to at least a portion of a signal transduction protein encoding nucleic acid molecule according to conditions described in Sambrook et al., ibid.

As guidance in determining what particular modifications can be made to any particular nucleic acid molecule, one of skill in the art should consider several factors that, without the need for undue experimentation, permit a skilled artisan to appreciate workable embodiments of the present invention. For example, such factors include modifications to nucleic acid molecules done in a manner so as to maintain particular functional regions of the encoded proteins including, a ligand binding site, a target binding site, a kinase catalytic domain, etc. Functional tests for these various characteristics (e.g., ligand binding studies and signal transduction assays such as kinase assays, and other assays described in detail herein and those known by those in the art) allows one of skill in the art to determine what modifications to nucleic acid sequences would be appropriate and which would not.

Transformation of a heterologous nucleic acid molecule (e.g., a heterologous cell surface receptor encoding a nucleic acid molecule) into a cell suitable for use in the present invention can be accomplished by any method by which a gene is inserted into a cell. Transformation techniques include, but are not limited to, transfection, retroviral infection, electroporation, lipofection, bacterial transfer and spheroplast fusion. Nucleic acid molecules transformed into cells suitable for use in the present invention can either remain on extra-chromosomal vectors or can be integrated into the cell genome.

Expression of a nucleic acid molecule of the present invention in a cell can be accomplished using techniques known to those skilled in the art. Briefly, the nucleic acid molecule is inserted into an expression vector in such a manner that the nucleic acid molecule is operatively joined to a transcription control sequence in order to be capable of effecting either constitutive or regulated expression of the gene when the gene is transformed into a host cell. Construction of desired expression vectors can be performed by methods known to those skilled in the art and expression can be in eukaryotic or prokaryotic systems. An expression system can be constructed from control elements, including transcription control sequences, translation control sequences, origins of replication, and other regulatory sequences that are compatible with a host cell, operatively linked to nucleic acid sequences using methods known to those of skill in the art. (see, for example, Sambrook et al., ibid.).

In one embodiment, a cell suitable for use in the present invention is transformed with a nucleic acid molecule encoding CD40, JNK and/or p38, as described in detail herein. In another embodiment of the present invention, a cell suitable for use in the present invention is transformed with a nucleic acid molecules encoding at least one type of intracellular signal transduction protein of the present invention. Preferred intracellular signal transduction protein encoding nucleic acid molecules include, but are not limited to, nucleic acid molecules encoding JNK, p38, MEKK, Jun, ATF, Myc protein, p38, PI-3 kinase, CDC42, Rho, Rac, JAK family of kinases (e.g. JAK1, JAK2, JAK3), STAT family of kinases, JNKK, Elk-1 and other Ets family members, PLCγ and intracellular calcium.

It is within the scope of the present invention that a cell can be transformed with both a nucleic acid molecule encoding at least one type of signal transduction molecule and a nucleic acid molecule encoding at least one type of cell surface receptor.

In one embodiment, the method of the present invention comprises contacting a cell with a putative regulatory compound. According to the present invention, putative regulatory compounds include compounds that are suspected of being capable of regulating CD40, JNK and/or p38 activity. The term "activity" refers to any stage of activation of a signal transduction molecule by, for example, conformational change of a molecule which results in the acquisition of catalytic activity by the molecule; the phosphorylation of a molecule, thereby resulting in the acquisition or loss of catalytic activity by the molecule; or the translocation of a molecule from one region of a cell to another, thereby enabling the molecule to bind another molecule. The term "regulate" refers to controlling the activity of a molecule and/or biological function, such as enhancing or diminishing such activity or function.

Putative compounds as referred to herein include, for example, compounds that are products of rational drug design, natural products and compounds having partially defined signal transduction regulatory properties. A putative compound can be a protein-based compound, a carbohydrate-based compound, a lipid-based compound, a nucleic acid-based compound, a natural organic compound, a synthetically derived organic compound, an anti-idiotypic antibody and/or catalytic antibody, or fragments thereof. A putative regulatory compound can be obtained, for example, from libraries of natural or synthetic compounds, in particular from chemical or combinatorial libraries (i.e., libraries of compounds that differ in sequence or size but that have the same building blocks; see for example, U.S. Pat. Nos. 5,010,175 and 5,266,684 of Rutter and Santi, which are incorporated herein by reference in their entirety) or by rational drug design.

In a rational drug design procedure, the three-dimensional structure of a compound, such as a signal transduction molecule can be analyzed by, for example, nuclear magnetic resonance (NMR) or x-ray crystallography. This three-dimensional structure can then be used to predict structures of potential compounds, such as putative regulatory compounds by, for example, computer modelling. The predicted compound structure can then be produced by, for example, chemical synthesis, recombinant DNA technology, or by isolating a mimetope from a natural source (e.g., plants, animals, bacteria and fungi). Potential regulatory compounds can also be identified using SELEX technology as described in, for example, PCT Publication Nos. WO 91/19813; WO 92/02536 and WO 93/03172 (which are incorporated herein by reference in their entirety).

In particular, a naturally-occurring intracellular signal transduction molecule can be modified based on an analysis of its structure and function to form a suitable regulatory compound. For example, a compound capable of regulating the kinase domain of JNK can comprise a compound having similar structure to a residues 1–79 of the amino terminus of JNK. Such a compound can comprise a peptide, a polypeptide or a small organic molecule.

Putative regulatory compounds can also include molecules designed to interfere with CD40. For example, mutant CD40 can be created that interfere with the coupling of the receptor to intracellular signal transduction proteins. Alternatively, mutant CD40 can be created that interfere with the binding of CD40 ligand to CD40. Putative regulatory compounds can include agonists and antagonists of CD40. Such agonists and antagonists can be selected based on the structure of a naturally-occurring ligand to CD40.

The conditions under which the cell of the present invention is contacted with a putative regulatory compound, such as by mixing, are conditions in which the cell can exhibit JNK and/or p38 activity if essentially no other regulatory compounds are present that would interfere with such activity. Achieving such conditions is within the skill in the art, and includes an effective medium in which the cell can be cultured such that the cell can exhibit JNK and/or p38 activity. For example, for a mammalian cell, effective media are typically aqueous media comprising RPMI 1640 medium containing 10% fetal calf serum.

Cells of the present invention can be cultured in a variety of containers including, but not limited to, tissue culture flasks, test tubes, microtiter dishes, and petri plates. Culturing is carried out at a temperature, pH and carbon dioxide content appropriate for the cell. Such culturing conditions are also within the skill in the art. For example, for Ramos cells, culturing can be carried out at 37° C., in a 5% $CO_2$ environment.

Acceptable protocols to contact a cell with a putative regulatory compound in an effective manner include the number of cells per container contacted, the concentration of putative regulatory compound(s) administered to a cell, the incubation time of the putative regulatory compound with the cell, the concentration of ligand and/or intracellular initiator molecules administered to a cell, and the incubation time of the ligand and/or intracellular initiator molecule with the cell. Determination of such protocols can be accomplished by those skilled in the art based on variables such as the size of the container, the volume of liquid in the container, the type of cell being tested and the chemical composition of the putative regulatory compound (i.e., size, charge etc.) being tested.

In one embodiment of the method of the present invention, a suitable number of cells are added to a 96-well tissue culture dish in culture medium. A preferred number of cells includes a number of cells that enables one to detect a change in JNK activity using a detection method of the present invention (described in detail below). A more preferred number of cells includes between about 1 and $1 \times 10^6$ cells per well of a 96-well tissue culture dish. Following addition of the cells to the tissue culture dish, the cells can be pre-incubated at 37° C., 5% $CO_2$ for between about 0 to about 24 hours.

A suitable amount of putative regulatory compound(s) suspended in culture medium is added to the cells that is sufficient to regulate the activity of a CD40, JNK and/or p38 protein in a cell such that the regulation is detectable using a detection method of the present invention. A preferred amount of putative regulatory compound(s) comprises between about 1 nM to about 10 mM of putative regulatory compound(s) per well of a 96-well plate. The cells are allowed to incubate for a suitable length of time to allow the putative regulatory compound to enter a cell and interact with a signal transduction molecule. A preferred incubation time is between about 1 minute to about 48 hours.

In another embodiment of the method of the present invention, cells suitable for use in the present invention are stimulated with a stimulatory molecules capable of binding to CD40 of the present invention to initiate a signal transduction pathway and create a cellular response. Preferably, cells are stimulated with a stimulatory molecule following contact of a putative regulatory compound with a cell. Suitable stimulatory molecules can include, for example, antibodies that bind specifically to the extracellular domain of CD40 and CD40 ligand. Preferred stimulatory molecules include, but are not limited to, anti-human CD40 antibody G28-5, soluble gp39, membrane-bound gp39 (e.g. gp39 bound to the plasma membrane of a cell or gp39 incorporated into a synthetic lipid-based substrate such as a liposome or micelle) and mixtures thereof. A suitable amount of stimulatory molecule to add to a cell depends upon factors such as the type of ligand used (e.g., monomeric or multimeric; permeability, etc.) and the abundance of the receptor on a cell. Preferably, between about 1.0 nM and about 1 mM of ligand is added to a cell.

The method of the present invention include determining if a putative regulatory compound is capable of regulating JNK activation. Such methods include assays described in detail in the Examples section. The method of the present invention can further include the step of performing a toxicity test to determine the toxicity of a putative regulatory compound.

Another aspect of the present invention includes a kit to identify compounds capable of regulating CD40 regulation of JNK or p38 activity in a cell. Such a kit includes: (1) a cell comprising CD40 protein, and JNK and/or p38 protein; and (2) a means for detecting regulation of either the JNK or p38 protein. Such a means for detecting the regulation of JNK protein include methods and reagents known to those of skill in the art, for example, JNK activity can be detected using, for example, activation assays described in Example 2. Means for detecting the regulation of p38 protein also include methods and reagents known to those of skill in the art. Suitable cells for use with a kit of the present invention include cells described in detail herein. A preferred cell for use with a kit includes, a human cell.

The present invention also includes the determination as to whether a putative regulatory compound is capable of regulating a biological response in a mammal. Such a method entails administering a putative regulatory compound to an animal, such compound being shown, using an assay of the present invention, to regulate CD40, JNK and/or p38 activity in a cell. Such a determination is useful for determining conditions under which a putative regulatory compound can be administered to an animal as a therapeutic composition. Thus, it is within the scope of the present invention that those conditions stated herein for testing a compound in an animal can be used when administering a therapeutic composition of the present invention. In particular, a putative regulatory compound can be administered to an animal to determine if the compound is capable of regulating, for example, an inflammatory response, a response to an infectious agent, an autoimmune response, a metabolic response, a cardiovascular response, an allergic response and/or an abnormal cellular growth response in the animal. Acceptable protocols to administer putative regulatory compounds to test the effectiveness of the compound include individual dose size, number of doses, frequency of dose administration, and mode of administration. Determination of such protocols can be accomplished by those skilled in the art. A suitable single dose is a dose that is capable of altering a biological response in an animal when administered one or more times over a suitable time period (e.g., from minutes to days or weeks). Preferably, a dose comprises from about 1 nanogram of the compound per kilogram of body weight (ng/kg) to about 1 gram of compound per kilogram of body weight (gm/kg), more preferably 100 ng/kg to about 100 milligrams/kilogram (mg/kg), and even more preferably from about 10 micrograms of compound per kilogram of body weight to about 10 mg/kg. Modes of administration can include, but are not limited to, aerosolized, subcutaneous, rectally, intradermal, intravenous, nasal, oral, transdermal and intramuscular routes. A putative regulatory compound can be combined with other components such as a pharmaceutically acceptable excipient and/or a carrier, prior to administration to an animal. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Carriers are typically compounds that increase the half-life of a compound in the treated animal. Suitable carriers include, but are not limited to, polymeric controlled release vehicles, biodegradable implants, liposomes, bacteria, viruses, oils, esters, and glycols. Preferred controlled release formulations are capable of slowly releasing a composition of the present invention into an animal. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other controlled release vehicles of the present invention include liquids that, upon administration to an animal, form a solid or a gel in situ. Preferred controlled release vehicles are biodegradable (i.e., bioerodible).

In another aspect of the present invention, the present invention includes conducting a toxicity test on an animal to determine the toxicity of a putative regulatory compound. Toxicity tests for putative regulatory compounds can be performed, for example, on animals after a putative regulatory compound has been determined to have an effect at the cellular level on signal transduction, such as the regulation of cellular inflammatory responses. Such toxicity tests are within the skill of the art, and generally involve testing the toxicity of a compound in vivo or in vitro. A suitable method for testing the toxicity of a putative regulatory compound in vivo can involve scientifically controlled administration of the putative regulatory compound to a number of animals and a period of observance in which the effects of the compound on various aspects of the animal's biological functions (e.g., occurrence of tissue damage, functioning of organs and death) are noted. Suitable methods for testing the toxicity of a putative regulatory compound in vitro can involve scientifically controlled administration of the putative regulatory compound to a cell and subsequent measurement of cell function, cytotoxicity, or cell death. Cell function can be measured by any one of a wide range of assays which will be apparent to one of skill in the art, several of which are herein disclosed (e.g., tyrosine phosphorylation, calcium mobilization and phosphoinositide assays). Methods to measure cytotoxicity are well known in the art and include measurement of the ability to reduce chromogenic substrates such as the tetrazolium-based MTT or sulphorhodamine blue, ATP-bioluminescence assays and fluorescence assays, for example using the Fluorescent Green Protein, among many other readily available assays (see, for example, Bellamy, *Drugs* 44(5):690–708, 1992, which is incorporated herein by reference in its entirety). Methods to measure cell death include, for example, Coomassie blue staining, acridine orange staining, terminal deoxynucelotidyl transferase (TDT) assays for measuring DNA fragmentation, neutral red exclusion, and measuring changes in forward light scattering in a flow cytometer.

Another aspect of the present invention includes a method to regulate a cellular function selected from the group consisting of immunoglobulin heavy chain class switching, cytokine production or inflammatory cell activation, comprising regulating the activity of a protein including CD40, JNK and/or p38. Regulation of activity of such protein can be achieved by sequestering JNK and/or p38 protein in an inactive complex, regulating the ligand binding activity of CD40, regulating the phosphorylation of JNK and/or p38 protein, regulating the interaction between JNK and JNKK, regulating the ability of JNK to activate c-Jun, ATF-2, and Ets-1 and other Ets family members, regulating the interaction between p38 and MEK, regulating the ability of p38 to activate ATF-2, and Ets-1 and other Ets family members, regulating the expression of endogenous and/or heterologous nucleic acid molecules encoding a CD40, JNK and/or p38 protein, and combinations thereof.

Suitable compounds for sequestering a JNK protein in an inactive complex, include compounds that mimic the site at which JNK protein interacts with JNKK, referred to herein as an activation site JNK mimetope. Suitable compounds for sequestering a p38 protein in an inactive complex, include compounds that mimic the site at which p38 protein interacts with MEK, referred to herein as an activation site p38 mimetope.

Suitable compounds for regulating the interaction between JNK and c-Jun, ATF-2, or Ets-1 or other Ets family members comprise JNK target site mimetopes. Suitable compounds for regulating the interaction between p38 and ATF-2, or Ets-1 or other Ets family members comprise p38 target site mimetopes.

Suitable compounds for regulating the ligand binding activity of CD40 include CD40 antagonists of extracellular ligands to CD40.

Other suitable regulatory compounds of the present invention include pseudosubstrates for a regulatory kinase domains of JNK or p38, a JNK kinase domain mimetope, a p38 kinase domain mimetope and a mutated CD40, JNK or p38 protein. Pseudosubstrates of a JNK kinase domain include small organic molecules, peptides or polypeptides that are phosphorylated by a JNK kinase domain in a similar manner as a JNK substrate including c-Jun, ATF-2, or Ets-1 or other Ets family members. Similarly, pseudosubstrates of a p38 kinase domain include small organic molecules, peptides or polypeptides that are phosphorylated by a p38 kinase domain in a similar manner as a p38 substrate including ATF-2, or Ets-1 or other Ets family members.

Suitable methods for regulating the expression of endogenous and/or heterologous nucleic acid molecules encoding CD40, JNK and/or p38 protein include methods known to those in the art. For example, oligonucleotides for use in, for example, antisense-, triplex formation-, ribozyme- and/or RNA drug-based technologies can be used to reduce expression of endogenous nucleic acid molecules encoding CD40, JNK and/or p38 protein. The present invention, therefore, includes such oligonucleotides and methods to interfere with the production of CD40, JNK and/or p38 protein by use of one or more of such technologies. Appropriate expression vectors can be developed by those skilled in the art based upon the cell-type being transformed.

In accordance with the present invention, a "mimetope" refers to any compound that is able to mimic the ability of a regulatory reagent of the present invention. A mimetope can be a peptide that has been modified to decrease its susceptibility to degradation but that still retains regulatory activity. Other examples of mimetopes include, but are not limited to, protein-based compounds, carbohydrate-based compounds, lipid-based compounds, nucleic acid-based compounds, natural organic compounds, synthetically derived organic compounds, anti-idiotypic antibodies and/or catalytic antibodies, or fragments thereof having desired regulatory activity. A mimetope can be obtained by, for example, screening libraries of natural and synthetic compounds for compounds capable of altering the activity of CD40 or JNK, as disclosed herein. A mimetope can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes by, for example, computer modelling. The predicted mimetope structures can then be produced by, for example, chemical synthesis, recombinant DNA technology, or by isolating a mimetope from a natural source (e.g., plants, animals, bacteria and fungi).

Another aspect of the present invention comprises administering to an animal, a therapeutic composition capable of regulating a biological function including immunoglobulin heavy chain class switching, cytokine production or inflammatory cell activation. A therapeutic composition of the present invention is particularly useful for preventing or treating diseases involving undesired immunoglobulin and/ or cytokine production, or inflammatory cell activation. In particular, a therapeutic composition is useful for preventing or treating diseases involving an allergic or autoimmune response. Preferably, a therapeutic composition of the present invention is used to prevent or treat a disease, including, but not limited to, allergic hypersensitivity, asthma, rheumatoid arthritis, systemic lupus erythematosus (SLE), allergic rhinitis, atopic dermatitis and acute bronchopulmonary aspergillosis. A therapeutic composition is preferably administered to a cell having CD40 and more preferably to cells including, but not limited to, Pre-B cells, B lymphocytes, cancer cells, fibroblasts, Langerhans cells, epithelial cells monocytes and dendritic cells.

A variety of therapeutic compositions can be used to perform the regulation method of the present invention. Such therapeutic compositions include those compounds described in detail herein, in particular, compounds identified using a method of the present invention. A therapeutic composition of the present invention can be formulated in an excipient that the animal to be treated can tolerate. Examples of such excipients include those described in detail above. In order to regulate heavy chain class switching in a cell, a therapeutic composition of the present invention can be administered in vivo (i.e., in an animal) or ex vivo (i.e., outside of an animal, such as in tissue culture), in an effective manner such that the composition is capable of regulating heavy chain class switching.

An effective administration protocol (i.e., administering a therapeutic composition in an effective manner) comprises suitable dose parameters and modes of administration that result in prevention or treatment of a disease. Effective dose parameters and modes of administration can be determined using methods standard in the art for a particular disease. Such methods include, for example, determination of survival rates, side effects (i.e., toxicity) and progression or regression of disease. For example, the effectiveness of dose parameters and modes of administration of a therapeutic composition of the present invention can be determined by assessing response rates. Such response rates refer to the percentage of treated patients in a population of patients that respond with either partial or complete remission.

In accordance with the present invention, a suitable single dose size is a dose that is capable of preventing or treating an animal with a disease when administered one or more times over a suitable time period. Doses can vary depending upon the disease being treated. For example, in the treatment of hypersensitivity, a suitable single dose can be dependent upon the nature of the immunogen causing the hypersensitivity.

It will be obvious to one of skill in the art that the number of doses administered to an animal is dependent upon the extent of the disease and the response of an individual patient to the treatment. For example, in the case of allergic responses, the immunogenicity of a compound may require more doses than a less immunogenic compound. Thus, it is within the scope of the present invention that a suitable number of doses, as well as the time periods between administration, includes any number required to cause treat a disease.

Therapeutic compositions can be administered directly to a cell in vivo or ex vivo or systemically. Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189:11277–11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art. Topical delivery can be performed by mixing a therapeutic composition of the present invention with a lipophilic reagent (e.g., DMSO) that is capable of passing into the skin.

The following examples are provided for the purposes of illustration and are not intended to limit the scope of the present invention.

EXAMPLES

Example 1

This example describes the activation of ERK by ligation of surface IgM but not CD40.

The human Burkitt's lymphoma cell line Ramos was obtained from the American Type Culture Collection (Rockville, Md.), and cells were maintained in RPMI-1640 supplemented with 50 units/ml penicillin-streptomycin, 2 mM glutamine, and 10% FCS. Exponentially growing cells were used in all experiments.

A. Immunoblot Assays Using Ramos Cells

About $1 \times 10^6$ Ramos cells were separately treated with 10 $\mu$g/ml anti-IgM F(ab')2 goat anti-human IgM antibody (obtained from Zymed, San Francisco, Calif.) or 5 $\mu$g/ml anti-CD40 antibody (G28-5; obtained from Dr. E. A. Clark, Washington University, Seattle, Wash.) for 0, 1, 5, 15, 30 or 60 min. Ramos cells were also treated with phorbol 12-myristate 13-acetate (PMA; obtained from Sigma, St Louis, Mo.). Immunoblot analysis was performed on each of the samples using monoclonal anti-ERK2 antibody in the following method. The treated cells were lysed in 100 $\mu$l of lysis buffer (25 mM Tris-HCl, pH 7.6, 50 mM NaCl, 0.5% Na deoxycholate, 2% NP-40, 0.2% SDS, 1 mM PMSF, 50 $\mu$g/ml aprotinin, 50 $\mu$M leupeptin). Lysates were centrifuged for 10 min at 14,000 rpm in an Eppendorf microcentrifuge, 90 $\mu$l of supernatants were mixed with 30 $\mu$l of 4× Laemmli sample buffer. Samples were boiled for 5 min. Twenty $\mu$l of prepared samples were electrophoresed through a 12% SDS-PAGE gel, and proteins were transferred to nitrocellulose membranes. Membranes were incubated in blocking buffer (25 mM Tris-HCl, pH 8.0, 125 mM NaCl, 0.1% Tween 20, 2% BSA, 0.1% NaN$_3$) at 4° C. overnight, then monoclonal mouse anti-ERK2 antibody (1:2000; obtained from Upstate Biotechnology Incorporated, Lake Placid, N.Y.) was added to the blocking buffer, and blots were incubated for an additional 2 hours at room temperature. The blots were washed three times in TBST (25 mM Tris-HCl, pH 8.0, 125 mM NaCl, 0.025% Tween 20) and incubated with AP-conjugated goat anti-mouse Ig (1:10000 in TBST; obtained from Promega, Madison, Wis.) for 1 hour at room temperature. The blots were washed three times in TBST and developed with the colorogenic substrates BCIP and NBT (Promega protoblot AP system).

The results from the immunoblot indicated that the untreated samples contained a single band (42 kD) reactive with anti-ERK2 antibody (lane 0'). In samples treated with PMA (100 ng/ml) or anti-IgM for 20 min, a second band with immunoreactivity to anti-ERK2 antibody appeared (lane PMA and anti-IgM lane 1'–60'). This lower mobility form represents the activated form due to phosphorylation. The samples treated with anti-CD40 demonstrated only a single band throughout the time course, thus indicating no lower mobility shift in $p42^{erk2}$. These data indicate that anti-IgM antibody activates $p42^{erk2}$ but anti-CD40 antibody fails to activate $p42^{erk2}$.

B. Immunoblot Assays Using Tonsillar Cells

The procedure of step A was repeated except using lysates from freshly isolated tonsillar B cells (prepared from tonsils as described in Takase et al., *J. Cell Physiol.* 162:246–255, 1995). Following treatment with 5 μg/ml anti-CD40 for the indicated times also showed no shift in ERK2 mobility.

B. ERK Kinase Assay

Kinase activity was evaluated using $EGFRF_{662-681}$ peptide as a substrate as described previously (Franklin et al., *J. Immunol.* 153:4890–4898, 1994). Following stimulation, $10^6$ cells were lysed in 75 μl of lysis buffer (70 mM β-glycerophosphate, pH 7.2, 100 mM $Na_3VO_4$, 2 mM $MgCl_2$, 1 mM EGTA, 0.5% Triton X-100, 5 μg/ml leupeptin, 2 μg/ml aprotinin and 1 mM DTT) and placed on ice for 15 min. Cell lysates were centrifuged at 14,000 rpm for 10 min and 20 μl of supernatant were removed and mixed with 20 μl of 2×kinase buffer (50 mM β-glycerophosphate, pH 7.2, 100 mM $Na_3VO_4$, 20 mM $MgCl_2$, 50 mg/ml IP-20, 1 mM EGTA, 400 μM $EGFR_{662-681}$ peptide, 200 μM ATP and 0.225 mCi/ml[γ-$^{32}$P] ATP [ICN Biochemicals, Costa Mesa, Calif.]). After 15 min at 30° C., 10 μl of 250 mM EDTA was added, and 45 μl of the reaction mixture was spotted onto P-81 phosphocellulose paper (Whatman, Clifton, N.J.). The papers were washed four times (5 min each) in 400 ml of 75 mM phosphoric acid and then radioactivity bound to the filter paper was determined by liquid scintillation counting. The assay system contained both EGTA (1 mM) and IP-20 (25 mg/ml), reagents that should effectively inhibit PKC, calcium/calmodulin, and cAMP-dependent kinases.

The results (shown in FIG. 1) indicate the kinase activity of samples treated with 100 ng/ml PMA for 20 min and 10 μg/ml anti-IgM for 5 min were about 30,000 counts per minute compared with samples from unstimulated (control) cells (about 10,000 cpm) or cells treated with 1 min (about 15,000 cpm), 5 min (about 17,000 cpm), or 10 μg/ml anti-CD40 for 20 min (about 15,000 cpm). The data represent incorporation of $^{32}$p (±SD) from separately prepared duplicate samples from two independent experiments. Statistically significant differences from untreated (0') samples are represented by an asterisk (*) (p <0.05).

The results confirm the results obtained in the immunoblot experiments. Activation of $p42^{erk2}$ by anti-IgM was confirmed by increases in $EGFR_{662-681}$ peptide phosphorylation. In contrast, the addition of anti-CD40 antibody at concentrations up to 10 μg/ml, failed to activate $p42^{erk2}$ in Ramos cells. Furthermore, we confirmed that anti-CD40 failed to activate $p42^{erk2}$ in freshly isolated tonsillar B cells.

Example 2

This example demonstrates that c-Jun kinase is activated by anti-CD40 antibody and soluble gp39 but not by anti-IgM antibody.

JNK activity was measured by solid-phase kinase assay using GST-c-Jun (1-79) as a substrate following treatment with anti-IgM antibody or anti-CD40 antibody (G28-5) in Ramos cells (three independent experiments) and tonsillar B cells (two independent experiments). GST-c-Jun (1-79) fusion protein was purified from bacterial lysates using GSH-Sepharose beads (Pharmacia Biotech, Uppsala, Sweden) at room temperature with gentle rocking using the method described in Galcheva-Gargova et al. (*Science* 265:806–808, 1994). Following stimulation, 3×10$^6$ cells were lysed in lysis buffer (20 mM Tris-HCl, pH 7.6, 250 mM NaCl, 3 mM EDTA, 3 mM EGTA, 0.5% NP-40, 2 mM $Na_3VO_4$, 1 mM DTT, 1 mM PMSF, 20 μg/ml aprotinin, 5 μg/ml leupeptin). The lysates were mixed with 10 μl of GST-c-Jun (1-79) coupled to GSH-Sepharose beads. The mixture was rotated at 4° C. for 3 hr in a microcentrifuge tube and pelleted by centrifugation at 14,000 rpm for 5 min. The pelleted beads were washed 2 times in lysis buffer and once in kinase buffer (20 mM Hepes, pH 7.5, 20 mM β-glycerophosphate, 10 mM $MgCl_2$, 1 mM DTT, 50 mM $Na_3VO_4$, 10 mM p-nitrophenyl phosphate), and then resuspended in 40 μl of kinase buffer containing 10 μCi of [γ-$^{32}$P]ATP. After 20 min at 30° C., the reaction was terminated by adding 4× Laemmli sample buffer and boiling for 3 min. Samples were resolved by 12% SDS-PAGE and subjected to autoradiography. Phosphate incorporation was determined by PhosphorImager (Molecular Dynamics, Sunnyvale, Calif.). The level of $^{32}$P incorporation (±SD) into the substrate is illustrated as the ratio of JNK activity to that of untreated samples.

Figure 2:
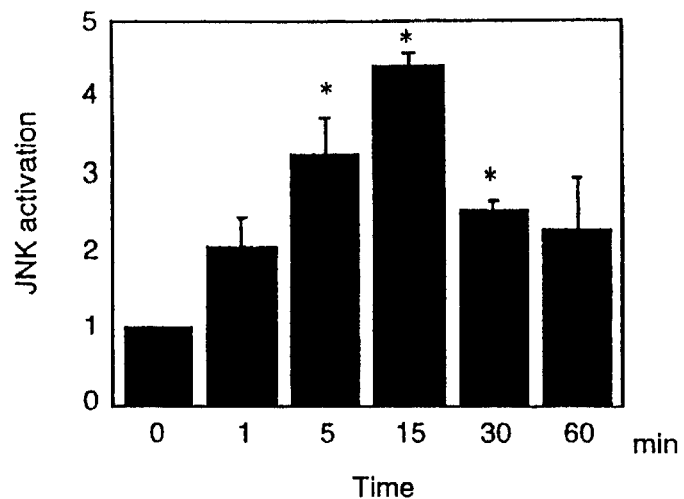
FIG. 2 illustrates the time course of JNK activation after treatment of Ramos cells with 1 μg/ml anti-CD40 antibody.

Results from a time course of JNK activation after treatment of Ramos cell with 1 μg/ml anti-CD40 antibody indicated a rapid and marked increase in JNK activation within 1 min of treatment with 1 μg/ml anti-CD40 antibody (FIG. 2), reached peak levels within 15 min and then began to decline by 30–60 min. Statistically significant differences from untreated (0') samples are represented by an asterisk (*) (p<0.05).

Figure 3:
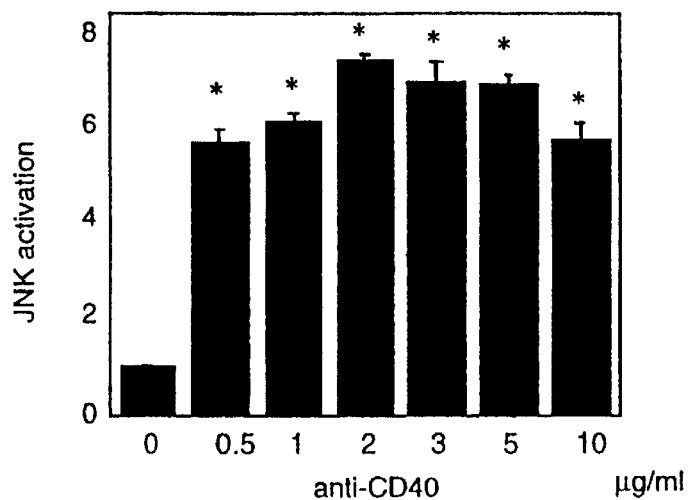
FIG. 3 illustrates the dose response of anti-CD40 antibody activated JNK in Ramos cells treated using various concentrations of anti-CD40 antibody for 15 min.

Results from a dose response study of anti-CD40 antibody-activated JNK in Ramos cells treated with various concentrations of anti-CD40 antibody for 15 min. indicated that, in the presence of 0.5 μg/ml anti-CD40 antibody, levels of $^{32}$P incorporation were five-fold higher than control samples (FIG. 3). JNK activity increased in a dose dependent fashion with peak levels (about seven-fold) observed at a concentration of 2–5 μg/ml antibody. Statistically significant differences from untreated (0') samples are represented by an asterisk (*) (p<0.05).

Figure 4:
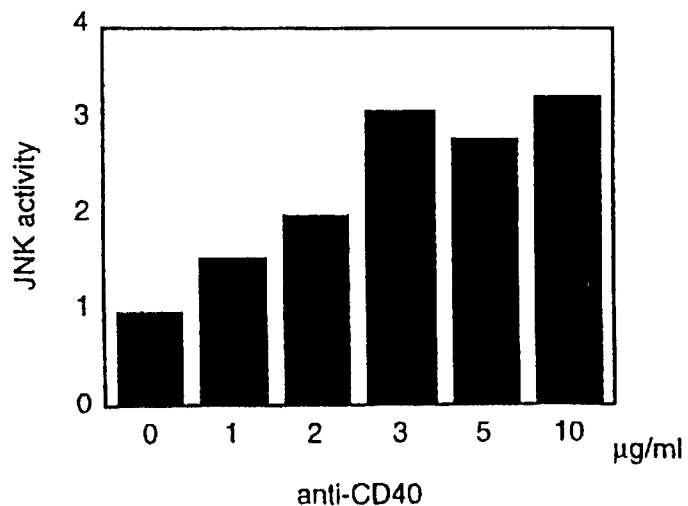
FIG. 4 illustrates the dose response of JNK activity to anti-CD40 antibody stimulation in tonsillar B cells treated for 15 min.

A dose-dependent response to anti-CD40 antibody was also detected in tonsillar B cells (FIG. 4). Throughout the dose-response curve lower levels of activation were observed in tonsillar B cells relative to Ramos cells, but both cell types clearly respond to CD40 ligation with a significant JNK activation.

Figure 5:
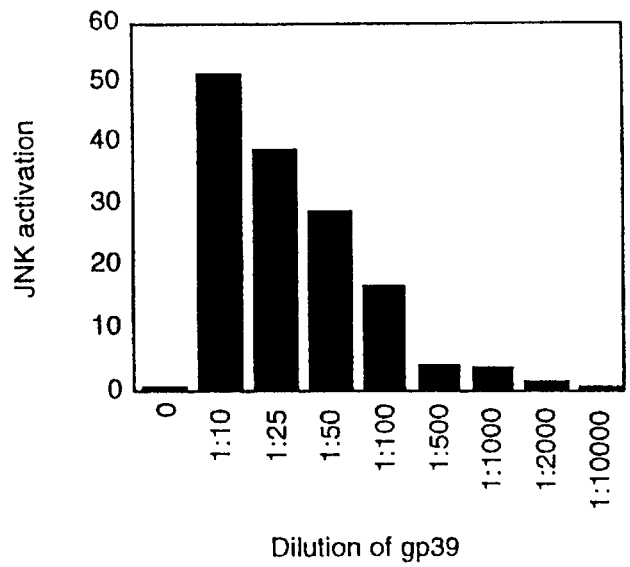
FIG. 5 illustrates activation of JNK using soluble gp39, in which dilutions of culture supernatants containing soluble gp39 were added to Ramos cells for 15 min.

Results from the treatment of Ramos cells for 15 min with dilutions of culture supernatants containing soluble gp39 (prepared as described in Hollenbaugh et al., *EMBO J.* 11:4313–4321, 1992) indicated that recombinant soluble gp39 also activated JNK in a dose-dependent fashion in Ramos cells (FIG. 5) and tonsillar B cells.

Results from blocking studies using dilutions of culture supernatants containing soluble gp39 that were pre-incubated with anti-gp39 antibody (2 μg/ml; mAb39-1.106; described in Bajorath et al., *Biochemistry* 34:1833–1844, 1995) for 5 min prior to addition to Ramos cells indicated that anti-gp39 antibody prevented activation of JNK by soluble gp39. JNK activation by UV irradiation was unaffected by the presence of the antibody. The anti-gp39 antibody failed to block UV-irradiation-induced activation of JNK.

Figure 6:
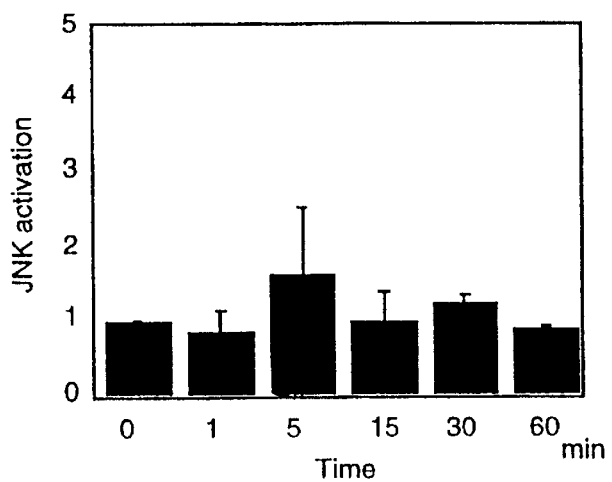
FIG. 6 illustrates the absence of stimulation of JNK activity in Ramos cells by anti-IgM antibody at different time periods.
Figure 7:
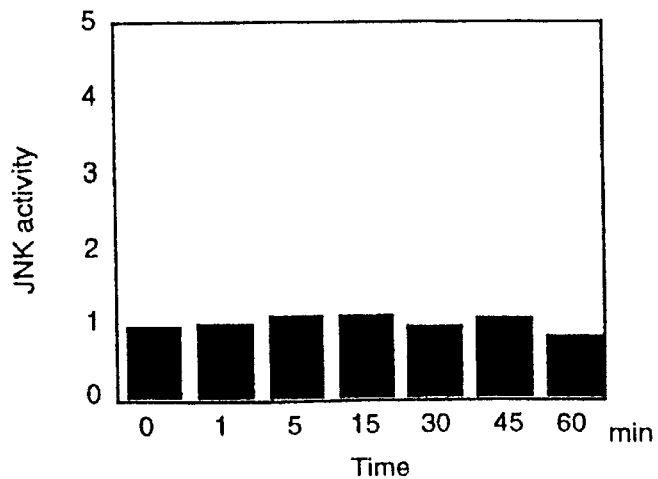
FIG. 7 illustrates the absence of stimulation of JNK activity in tonsillar B cells at different time periods.

Results from a time course cross-linking study using anti-IgM antibody indicated that JNK activity was not increased following surface IgM crosslinking even in the presence of 10 µg/ml anti-IgM antibody in Ramos cells (FIG. 6) and tonsillar B cells (FIG. 7).

Taken together, the results demonstrate that JNK is activated by anti-CD40 antibody but not anti-IgM antibody, indicating that anti-CD40 antibody activates JNK through a different signaling pathway than that which mediates ERK activation by anti-IgM antibody.

Example 3

This example demonstrates that anti-CD40 antibody activates JNK through a Ras-independent pathway.

Metabolically labeled ($^{32}$P)Ramos cells were untreated (control) or treated with 10 µg/ml anti-IgM or 5 µg/ml anti-CD40 for 1, 5 and 10 min, respectively. Ras was immunoprecipitated using the Y13-259 anti-Ras antibody, and radioactive GTP and GDP bound to Ras was measured as follows. Cells ($10^7$ cells) were labeled with $^{32}$P-orthophosphate for 16 hr, and then stimulated. Ras was immunoprecipitated using the Y13-259 anti-Ras antibody, and GTP was separated from GDP by thin layer chromatography as described (Downward et al., *Nature* 346:719–723, 1990). The radiolabeled nucleotides were visualized by autoradiography. Radioactivity was quantitated with a PhosphorImager and the GTP/GTP+(1.5) GDP ratios were calculated. The data were quantitated by PhosphorImager, and shown are the GTP/GDP+(1.5) GDP ratios (in percent) for each condition. The results represent three separate experiments. Statistically significant differences from untreated (0') samples are represented by an asterisk (*) ($p<0.05$).

Figure 8:
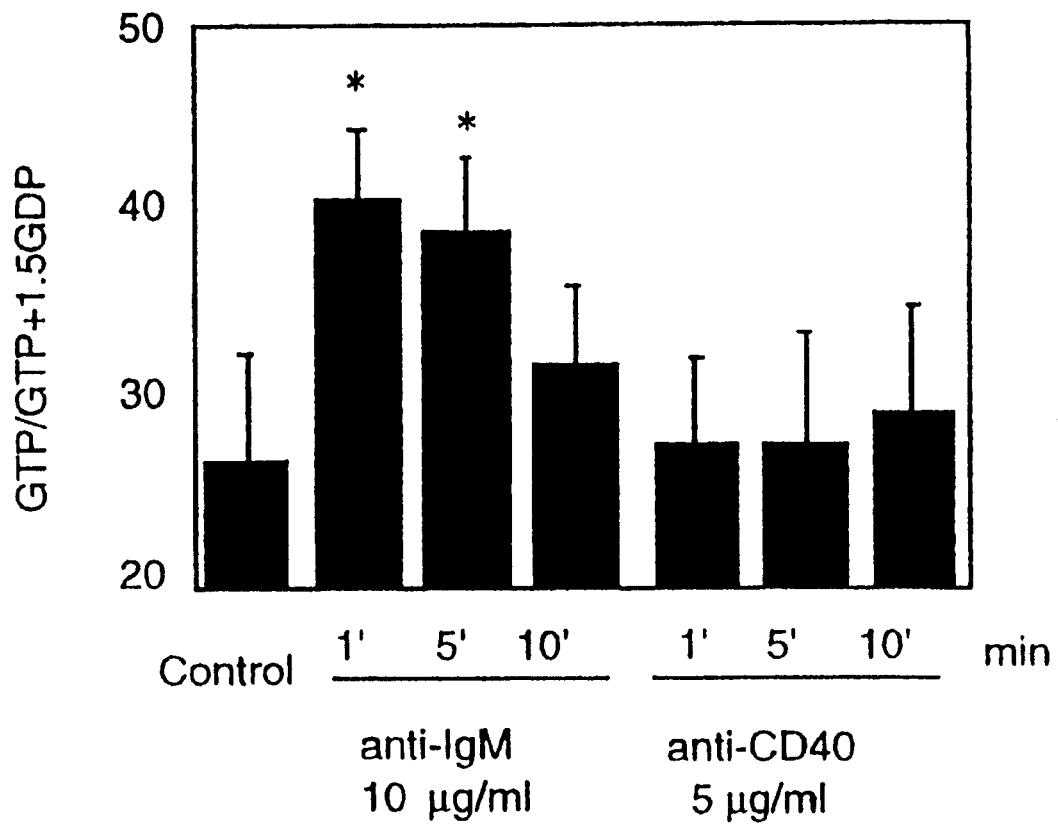
FIG. 8 illustrates the activation of Ras following treatment of cells with anti-IgM antibody but not after treatment with anti-CD40 antibody.

The results, shown in FIG. 8, indicate that treatment with anti-IgM antibody activated Ras. Anti-CD40 antibody treatment, however, failed to activate Ras at concentrations that were effective in JNK activation (described in Example 2). The results demonstrate that the signals transduced following CD40 engagement lead to JNK activation through a pathway that does not involve Ras activation.

Example 4

This example demonstrates that Raf-1 does not participate in the CD40-activated JNK pathway.

Ramos cells were untreated or treated with 100 ng/ml PMA, 10 µg/ml anti-IgM or 5 µg/ml anti-CD40 for 1, 2.5, 5, 10 or 20 min. Raf-1 was immunoprecipitated and a kinase assay was performed using the following method. Cells ($10^7$) were stimulated in RPMI 1640 medium, and then lysed in RIPA (10 mM sodium phosphate, pH 7.0, 150 mM NaCl, 2 mM EDTA, 1% sodium deoxycholate, 1% Nonidet P-40, 0.1% SDS, 1% aprotinin, 50 mM NaF, 200 mM Na$_3$VO$_4$, 0.1% 2-mercaptoethanol, 1 mM PMSF). The lysates were precleared by protein A-Sepharose beads for 30 min at 4° C. A purified polyclonal anti-Raf-1 antibody was added to the lysates (1:100; obtained from Santa Cruz Biotechnology, Santa Cruz, Calif.) and incubated for 90 min at 4° C. The immunocomplexes were collected by protein A-Sepharose beads. The beads were then washed 3 times in RIPA and 3 times in a buffer containing 10 mM PIPES, pH 7.0, 100 mM NaCl, 2 µg/ml aprotinin. A kinase mixture (40 µl) containing 10 mM PIPES, pH 7.0, 100 mM NaCl, 5 mM MnCl$_2$, 2 µg/ml aprotinin, 30 µCi of [γ-$^{32}$P]ATP and 100–200 ng of catalytically inactive MEK (KMMEK) was added to the beads. KMMEK was expressed and purified as described (Gardner et al., *Methods Enzymol.* 238:258–270, 1994). The samples were incubated for 30 min at 30° C. The kinase reaction was stopped by addition of 4× Laemmli sample buffer and boiling for 3 min. The proteins were resolved on 10% SDS-PAGE and transferred to a nitrocellulose membrane. The membrane was probed using the same anti-Raf-1 antibody and visualized as described above and subjected to autoradiography.

The results indicate that the levels of KMMEK phosphorylation following treatment with 5 µg/ml anti-CD40 antibody were not different than control samples, whereas cells treated with anti-IgM antibody resulted in increased KMMEK phosphorylation. To verify similar loading of immunoprecipitated Raf-1, an immunoblot was concomitantly performed using the same antibody as was used for the immunoprecipitates. The Raf-1 mobility shifts were consistent with the increased levels of kinase activity measured using KMMEK. The magnitude of anti-IgM antibody activation of Raf-1 was sufficient to activate ERK2 similarly as PMA. Raf-1, which is an efficient activator of the ERK pathway, is not measurably activated during JNK activation in response to CD40 ligation.

Example 5

This example demonstrates that anti-CD40 antibody activates MEKK protein.

Ramos cells were treated with 2 µg/ml anti-CD40 antibody for 0, 0.5, 1, 2.5, 5 or 10 min. MEKK was immunoprecipitated and a kinase assay was performed using the following methods. Following stimulation, 5×$10^6$ cells were lysed in 400 µl of extraction buffer (1% Triton X-100, 10 mM Tris-HCl [pH 7.4], 5 mM EDTA, 50 mM NaCl, 50 mM NaF, 0.1% bovine serum albumin, aprotinin [20 µg/ml], 1 mM PMSF, and 2 mM Na$_3$VO$_4$). The lysates were centrifuged for 10 min at 14,000 rpm and pellets were discarded. The supernatants were incubated with the rabbit MEK kinase (MEKK) antisera (1:100 dilution) raised against the MEKK NH2-terminal fusion protein (described in Lange-Carter et al., *Methods Enzymol.* 255:290–301, 1995) for 2 hr at 4° C. The immune complexes were collected by protein A-Sepharose beads. The beads were then washed twice in RIPA buffer and three times in a buffer containing 10 mM PIPES, pH 7.0, 100 mM NaCl, 2 µg/ml aprotinin. A kinase mixture (40 µl) containing 10 mM PIPES, pH 7.0, 100 mM NaCl, 5 mM MnCl$_2$, 2 µg/ml aprotinin, 30 µCi of [γ-$^{32}$P]ATP and 0.5 µl of recombinant JNK activating protein kinase (JNKK; described in Lin et al., *Science* 268:286–290, 1995) as a substrate was added to the beads. The samples were incubated for 30 min at 30° C. The kinase reaction was stopped by addition of 4× Laemmli sample buffer and boiling for 3 min. The proteins were resolved on 10% SDS-PAGE, transferred to a nitrocellulose membrane and subjected to autoradiography. Phosphate incorporation was quantitated by PhosphorImager.

Figure 9:
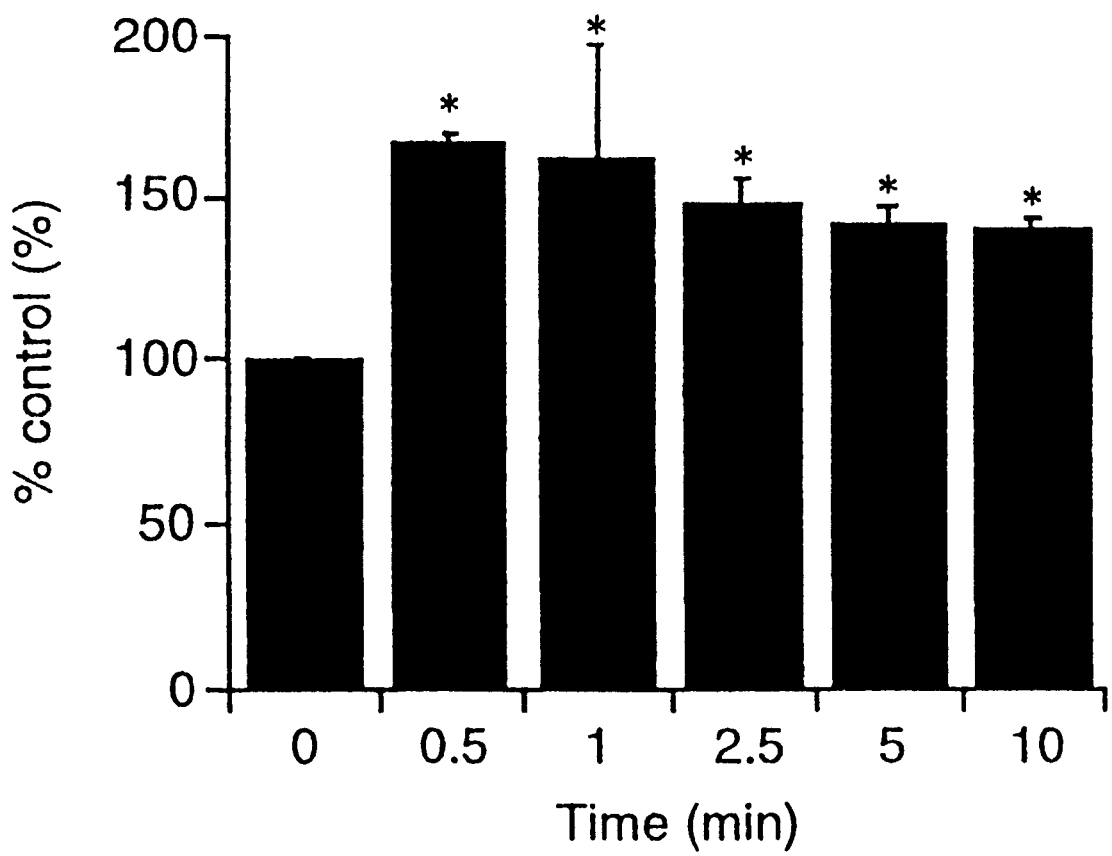
FIG. 9 illustrates the activation of MEKK protein following treatment with anti-CD40 antibody.

The results of $^{32}$P incorporation into JNKK are illustrated in FIG. 9 as the ratio of MEKK activity of treated to that of untreated samples. Statistically significant differences from untreated (0') samples are represented by an asterisk (*) ($p<0.05$). MEKK was activated rapidly, reaching maximal stimulation by 30 sec after anti-CD40 antibody treatment, and then decreased gradually with time. Immunoblots of the immunoprecipitated MEKK with the anti-MEKK polyclonal antibody that were used for immunoprecipitation revealed similar amounts of a 98 kD MEKK protein for each time point. These data indicate that an MEKK is present in B-lymphoblastoid cells which regulates the JNK pathway and is activated in response to CD40 ligation.

Example 6

This example demonstrates that anti-CD40 antibody rescues apoptosis induced by anti-IgM antibody.

Ramos cells were untreated (control) or treated with 10 µg/ml anti-IgM antibody or 2 µg/ml anti-CD40 antibody; co-stimulation of cells consisted of a 30 min preincubation with anti-CD40 antibody followed by an incubation with anti-IgM antibody. After 18 hr culture, DNA breaks derived from anti-IgM induced apoptosis were evaluated using an in situ TdT assay using the method as follows. For detection of DNA strand breaks in individual cells, an in situ terminal deoxynucleotidyl transferase (TdT) assay was employed based on the method of Gorczyca et al. (*Cancer Res.* 53:3186–3192, 1993) with minor modifications. Cells were treated for 18 hr as indicated. About $10^6$ cultured cells were washed in PBS and suspended in 500 µl of PBS. Paraform (4%, 170 µl) was added and the mixture was stored on ice for 15 min. Cells were then washed in cold PBS and fixed with 70% ethanol at −20° C. for an hour. Following washing in cold PBS, the cells were resuspended in TdT reaction buffer (0.1 M potassium cacodylate, pH 7.2, 2 mM $CoCl_2$, 0.2 mM DTT, 20 U TdT, 2 nmol fluorescein-dUTP, 10 mg/ml BSA). After 30 min at 37° C., cells were washed once in 0.2% BSA/PBS and fluoresce staining was evaluated on an EPICS Profile (Coulter, Hialeah, Fla.).

$p42^{erk2}$ (5 min following treatment) and JNK activation (15 min following treatment) were evaluated under identical conditions as described in Example 1. The level of $^{32}P$ incorporation (±SD) from two independent experiments was evaluated by PhosphorImager, and then plotted as the ratio of JNK activation to that of untreated samples. Statistically significant differences from untreated samples are represented by an asterisk (*) ($p<0.05$).

The results indicate that DNA breaks were detected in 64.2% of Ramos cells, 18 hr following treatment with 10 µg/ml anti-IgM antibody, whereas there was no shift in fluorescence intensity in control (untreated) cells or in cells treated with 2 µg/ml anti-CD40 antibody. In the presence of 2 µg/ml anti-CD40 antibody preincubated for 30 min prior to the addition of anti-IgM antibody, however, DNA breaks induced by anti-IgM antibody were reduced to 3.5% of the cells. Under identical conditions, an immunoblot using anti-ERK2 monoclonal antibody indicated the mobility shift in $p42^{erk2}$ protein, 5 min following treatment with 10 µg/ml anti-IgM antibody in the presence of 2 µg/ml anti-CD40 antibody preincubated for 30 min. In addition, JNK activity, measured by solid phase kinase assay using GST-c-Jun fusion protein, was increased 15 min following treatment with anti-CD40 antibody in the presence of anti-IgM antibody. Thus, CD40 ligation does not effect $p42^{erk2}$ activation by sIgM and sIgM ligation does not effect CD40 activation of JNK.

Example 7

This example describes the activation of p38 by CD40 ligation.

Neutrophils isolated by the plasma percoll method as previously described (Haslett, C., *Am. J. Pathol.* 119, 101–110; 1985) were resuspended at about 25×$10^6$ cells/ml in KRPD containing 0.1% Human Heat Inactivated Platelet-Poor Plasma, 1 mM PMSF, 10 µg/ml leupeptin and 10 µg/ml aprotinin. About 25×$10^6$ PMN were preincubated for 30 minutes at 37° C., then stimulated with 100 ng/ml LPS for varying time intervals and reactions terminated by a 20 second centrifugation at 15,000 rpm. Cell pellets were lysed with 500 µl cold RIPA (50 mM Tris pH=7.2, 150 mM NaCl, 1.1% SDS, 0.1% sodium deoxycholate, 1% Triton-X-100, 10 mM sodium pyrophosphate, 25 mM B glycerophosphate, 1 mM sodium orthovanadate and 2.1 µg/ml aprotinin), and centrifuged at 15,000 for 10 minutes at 4° C. Triton soluble lysates were initial precleared with Protein A Sepharose for 30 minutes at 4° C., followed by Protein A Sepharose immunoprecipitation with 5 µl/sample polyclonal antibodies specific for p38 and 15 µl of bead suspension, for 120 minutes at 4° C. Beads were washed once in RIPA and twice in PAN (10 mM Pipes, 100 mM NaCl, pH=7.0, and 21 µg/ml aprotinin). Beads were resuspended 25 µl kinase mix containing 20 mM Hepes, pH=7.6, 200 mM $MgCl_2$, 20 µM ATP, 20 µCi [$^{32}P$]γ-ATP, 2 mM dTT, 100 µM sodium orthovanadate, 25 mM B-glycerophosphate (pH=7.2) and a peptide comprising amino acids 1–110 of ATF-2. The samples were incubated for 15 minutes at 30° C. with frequent mixing. Reactions were terminated with 2× Laemelli buffer and after boiling, proteins were separated by SDS-PAGE, with quantification of activity by autoradiography and phosphorimaging, and qualitative analysis of enzyme presence and phosphorylation by Western Blotting.

Figure 10:
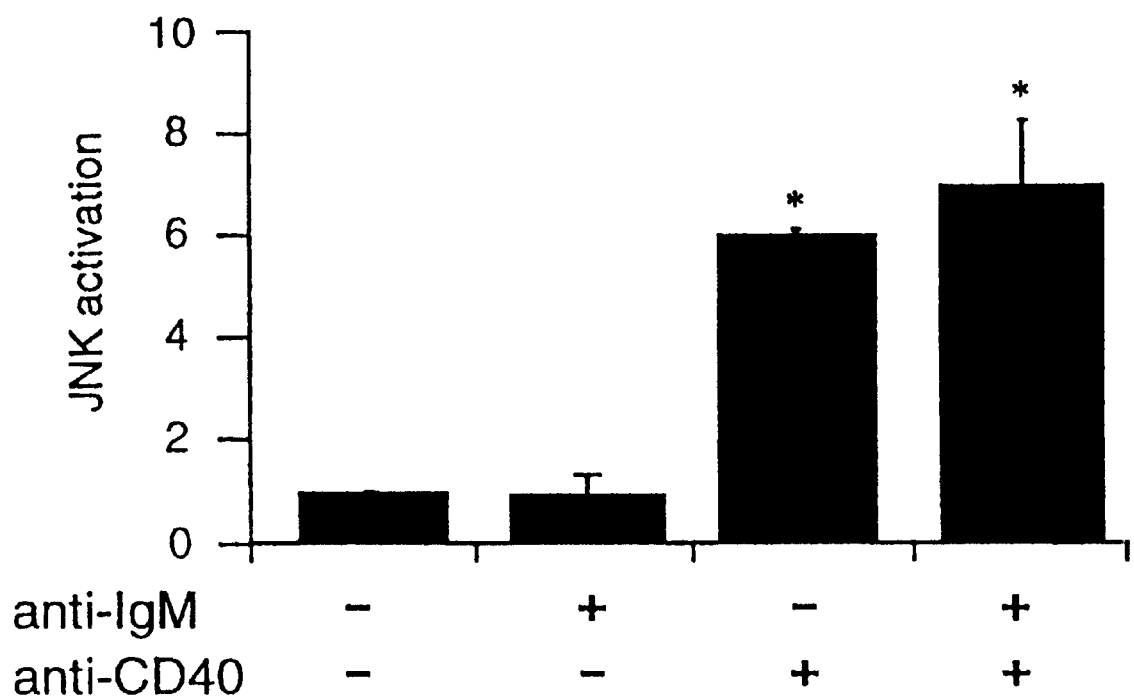
FIG. 10 illustrates the activation of JNK in Ramos cells by anti-IgM or anti-CD40 antibody alone, or after preincubation with anti-CD40 antibody followed by incubation with anti-IgM antibody.
Figure 11:
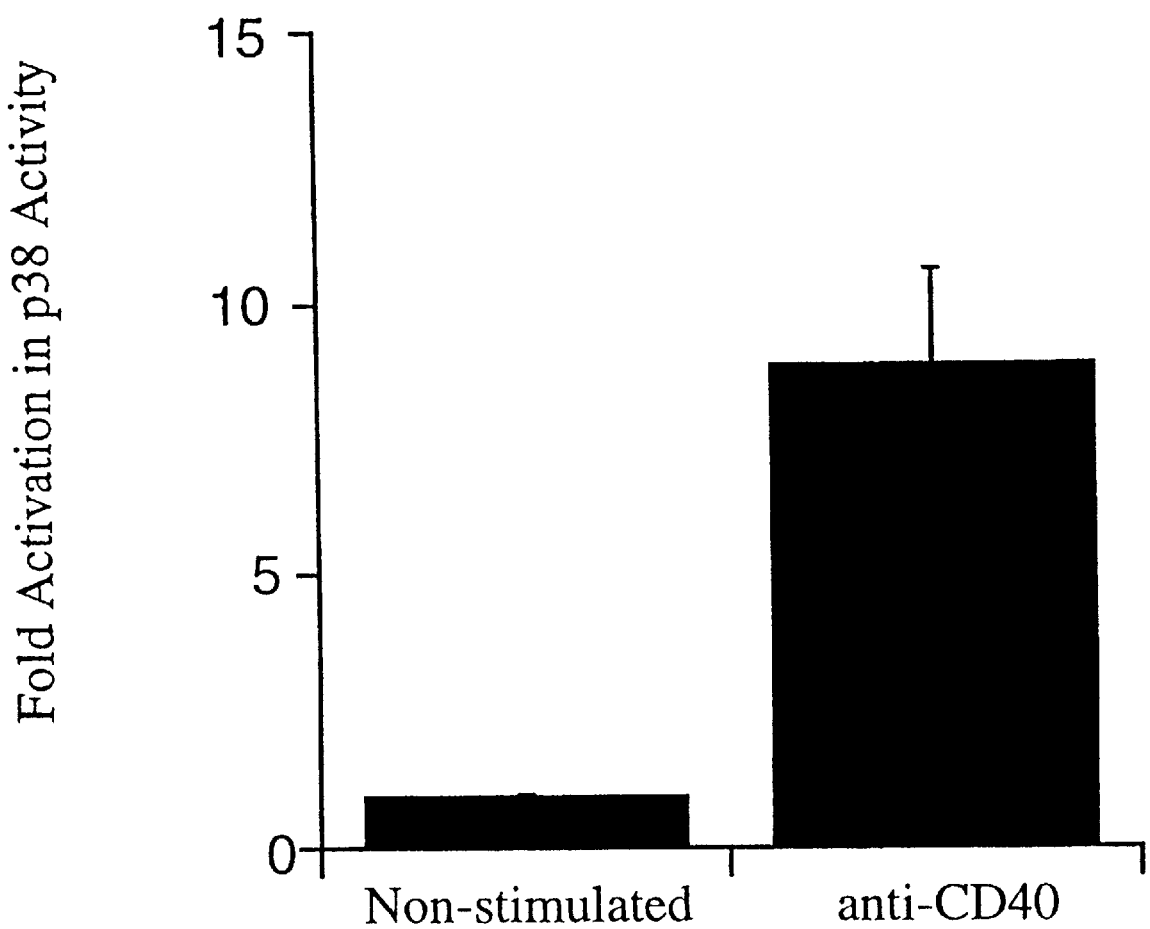
FIG. 11 illustrates activation of p38 in the presence or absence of anti-CD40 antibody.

The results are shown in FIG. 10 and indicate that p38 MAP kinase is activated in neutrophils by lipopolysaccharide.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. A method to identify a compound that regulates CD40 activation of Jun Kinase (JNK) in a cell, comprising:
   (a) contacting a putative regulatory compound with a cell that expresses CD40 and Jun kinase;
   (b) contacting said cell simultaneously or after said step (a) with a stimulatory compound selected from the group consisting of CD40 ligands, gp39, and antibodies that specifically bind to CD40, wherein said stimulatory compound stimulates CD40 signal transduction resulting in activation of Jun kinase, said contacting occurring under conditions in which, in the absence of said stimulatory compound, said Jun kinase is not activated;
   (c) assessing the ability of said putative regulatory compound to regulate CD40-mediated activation of said Jun kinase, said activation being determined by measurement of an activity selected from the group consisting of phosphorylation of Jun kinase and phosphorylation of a substrate by Jun kinase;
   wherein an increase or decrease in said activation of Jun kinase in the presence of said putative regulatory compound, as compared to in the absence of said putative regulatory compound, indicates that said compound regulates CD40-mediated activation of Jun kinase.

2. The method of claim 1, wherein said assessment step comprises determining the ability of said Jun kinase to phosphorylate a protein selected from the group consisting of c-Jun, ATF-2, Ets-1 and other Ets family members in said cell.

3. The method of claim 1, wherein said stimulatory compound is a ligand of CD40.

4. The method of claim 1, wherein said gp39 is selected from the group consisting of soluble gp39 and membrane-bound gp39.

5. The method of claim 1, wherein said cell is a mammalian cell.

6. The method of claim 1, wherein said cell is selected from the group consisting of a primate, a mouse and a rat cell.

7. The method of claim 1, wherein said cell is selected from the group consisting of Pre-B cells, B lymphocytes, cancer cells, fibroblasts, Langerhans cells, epithelial cells monocytes and dendritic cells.

8. The method of claim 1, wherein said putative regulatory compound is selected from the group consisting of a protein-based compound, a carbohydrate-based compound, a lipid-based compound, a nucleic acid-based compound, a natural organic compound, a synthetically derived organic compound, an anti-idiotypic antibody and/or catalytic antibody, or fragments thereof.

9. The method of claim 1, wherein said putative regulatory compound is selected from the group consisting of a small organic molecule, a peptide and a polypeptide.

* * * * *